United States Patent [19]

Dekmezian et al.

[11] Patent Number: 5,039,614
[45] Date of Patent: Aug. 13, 1991

[54] METHOD AND APPARATUS FOR COLLECTING SAMPLES FOR ANALYSIS OF CHEMICAL COMPOSITION

[76] Inventors: Armenag Dekmezian, 814 E. Broad St., Westfield, N.J. 07090; Tetsuya Morioka, 4-3-335 Nishitsurugaoka 1-chome, Ooimachi, Iruma-gun, Saitama-ken, Japan

[21] Appl. No.: 539,380

[22] Filed: Jun. 15, 1990

Related U.S. Application Data

[63] Continuation of Ser. No. 207,770, Jun. 16, 1988, abandoned.

[51] Int. Cl.⁵ .................................................. G01N 35/00
[52] U.S. Cl. ........................................ 436/43; 436/47; 436/174; 422/63; 422/64
[58] Field of Search .................................. 422/63–67, 422/78; 436/43, 47, 85, 174; 435/301, 312

[56] References Cited

U.S. PATENT DOCUMENTS

| | | | |
|---|---|---|---|
| 3,788,479 | 1/1974 | Szakasits | 422/78 |
| 4,376,391 | 3/1983 | Brunnee | 422/64 |
| 4,552,723 | 11/1985 | Adams et al. | 422/66 |
| 4,604,363 | 8/1986 | Newhouse et al. | |
| 4,659,014 | 4/1987 | Soth et al. | 239/102.2 |
| 4,820,044 | 4/1989 | Crighton et al. | 422/64 |

OTHER PUBLICATIONS

C. C. Johnson and L. T. Taylor, *Anal. Chem.*, 56, 2642–2647 (1984).
C. M. Conroy, P. R. Griffiths, K. Jinno, *Anal. Chem.* 57, 822–825 (1985).
L. Wild, T. R. Ryle, etc., *J. Polymer Science: Polymer Physics Ed.*, 20, 441–455 (1982).
H. Sato et al, *Macromolecules*, 19, 2613 (1986).
S. Mori and T. Suzuki, *J. of Liquid Chrom.*, 4 (10), 1685 (1981).

*Primary Examiner*—Robert J. Warden
*Assistant Examiner*—D. John Griffith, Jr.
*Attorney, Agent, or Firm*—Kenneth R. Schaefer

[57] ABSTRACT

An automated, on-line solvent elimination interface system is described for use in characterizing the Composition Distribution (CD) of unknown materials emerging from a fractionating unit or a process stream. Fractionated samples to be analyzed, such as a polymer, in highly diluted form in one or more solvents, are provided by a fractionation unit such as a gel permeation chromatograph (GPC), a high pressure liquid chromatograph (HPLC), or a field flow fractionator (FFF). A number of discharges of each particular fraction are supplied to individual collection units within the interface system under controlled conditions of flow rate, temperature and pressure (vacuum) such that the solvents are flash-evaporated at the collection unit. A sufficient solid residue is built up on the collection unit for analysis by, for example, a Fourier transform infrared (FTIR) analyzer.

9 Claims, 5 Drawing Sheets

METHOD AND APPARATUS FOR COLLECTING SAMPLES FOR ANALYSIS OF CHEMICAL COMPOSITION

This is a continuation of application Ser. No. 207,770, filed 6/16/88.

BACKGROUND OF THE INVENTION

On-line analysis of the chemical composition of a solute in a carrier medium (e.g., a solvent) combination has been accomplished using various known techniques, such as a gel permeation chromatograph (GPC) coupled to an ultraviolet (UV) spectrometer. Generally, the success of such a technique depends on how well the solutes can be differentiated from the carrier medium. This differentiation has been relatively easy in most cases, but there are cases in which the carrier medium seriously interferes with the on-line analysis of the solute, rendering a particular analysis technique less useful than desired.

For example, in flow-thru high pressure liquid chromatographic (HPLC) systems coupled to a Fourier transform infrared (FTIR) spectrometer, the chromatographic solvent often interferes with the detection of the solute. Therefore, various flow-thru cells (e.g., see C.C. Johnson and L.T. Taylor, *Anal. chem.*, 56, 2642-2647 (1984)) as well as interfaces to eliminate the solvent prior to analysis (e.g., see C.M. Conroy, P.R. Griffiths, and K. Jinno, *Anal. Chem.*, 57, 822-825 (1985)) have been designed. Eliminating low-boiling point solvents such as hexane is easy to accomplish, but not so with water or higher-boiling organic solvents. With high boiling point solvents such as trichlorobenzene (TCB), which is a common solvent in the analysis of polymers by gel permeation chromatography (GPC), the situation is one of the worst. Consequently, on-line polymer composition analysis in a TCB solvent system by GPC/FTIR has so far remained in the realm of concept only. Similarly, FTIR as a powerful and versatile analytical tool for HPLC, GPC and process analyzers has been limited in its application because of the solvent or process interference problems.

Ideally, to eliminate the solvent-solute interference problems, whether in a GPC experiment or in continuous process control, one would like to eliminate the solvent altogether. If a technique can eliminate TCB, then it readily may be used to eliminate substantially any other chromatographic or process solvent.

Overcoming the above mentioned problem in high-temperature (HT) GPC would benefit studies aimed at determining composition distributions (CD) in polymers (e.g.,L. Wild, T.R. Ryle, D.C. Knobeloch, and I.R. Peat, *J. Polymer Science: Polymer Physics Edition*, 20 441-455 (1982)). CD is the change in comonomer composition of polymer chains as a function of their molecular weight (MW). Most CD studies of crystalline or amorphous polymers have depended on large-scale fractionation or cross-fractionation, often followed by a slow solvent-stripping step to prepare the fractions for subsequent analytical measurements. Only in favorable cases, such as in semicrystalline polymers, where a relationship may be established between comonomer content and melting temperature has the need for an on-line composition detector not been essential. In contrast, amorphous polymers cannot benefit from such empirical relationships. Consequently, most separations have depended on solvent/non-solvent fractionations (e.g., H. Sato et al, *Macromolecules*, 19, 2613 (1986)). These operations are very tedious and time-intensive, and although the individual steps can be automated to reduce manpower requirements (D.L. Newhouse, R.G. Wheeler, and R.H. Waltz, U.S. Pat. No. 4,604,363 (1986)), the time-intensive nature of the analysis still remains a big hurdle to be overcome. Recent advances in HT-GPC-UV have been used for composition analysis (e.g., S. Mori and T. Suzuki, *J. of Liquid Chrom.*, 4(10), 1685 (1981)), but the limitations imposed on the choice of solvent and the requirement that the polymer or solute must have a UV-active group restrict the applicability of this technique. Although FTIR is a less sensitive tool than UV, it is by far the more powerful structural tool because of its superior selectivity in terms of chemical species differentiation.

Another area where FTIR would be of tremendous importance is in the area of on-line analysis of liquid process streams, regardless if the stream is heterogeneous in nature or if the solutes are UV-inactive. The essential question is how to eliminate the solvent on-line for subsequent, automated on-line or off-line analytical measurements such as by FTIR.

SUMMARY OF THE INVENTION

In accordance with the present invention, methods and apparatus are provided which are particularly suitable for determining the compositional distribution (CD) of unknown materials such as polymers using a fractionation unit which employs a high boiling point solvent (such as TCB). To that end, an interface system is provided between such a fractionation unit (typically a GPC unit) and an analyzer unit such as a Fourier transform infrared (FTIR) analyzer. The interface system comprises a vacuum oven, the temperature and pressure of which are adjusted depending on the boiling point/vapor pressure characteristics of the solvent or solvent mixture that is to be eliminated. The oven may be configured in various ways. One is to equip it with a carousel-type programmable fraction collector having a discrete number of plates or hollowed dishes formed of potassium bromide (KBr). Another is to use a continuous collector which may be used, for instance, as an on-line plant stream (liquid phase) analyzer. In that case, the device would be separated into two differentially pumped chambers; one for collection of solvent-free samples and the other for on-line analysis (e.g. by FTIR or near-infrared fiber optic systems). Either way, the effluent from a fractionator unit is supplied as droplets and, as each droplet falls on the fraction collector, the solvent is flashed off immediately, leaving behind a residue. The process may be repeated as many times as desired before moving to the next collector position. Either during or after the collection step, the compositions of the fractions are determined automatically using a chosen microanalytical technique.

For safety reasons, it is preferable that the interface system have no exposed heating elements. Pressure and temperature are regulated so that when a solution droplet comes in contact with the collecting medium on a fraction collector (e.g., infrared window-dish), the solvent flash evaporates, leaving behind a residue. In the case of high-boiling point solvents such as trichlorobenzene, an additional stream of preheated nitrogen or other inert gas blowing over the collection site helps smooth the flash evaporation and eliminates potential splashing problems during the collection step.

Splashing could occur, for example, if the oven temperature is too high or too low for a given pressure. The droplet size may also play a role, depending on the physical properties of the droplet such as surface tension. Splashing may be minimized using different tip geometries to control droplet size, adjusting the flow and/or temperature of the inert gas blown onto the collection site, and/or adjusting the gap between the effluent tip and the collecting plate. Under such conditions, the gap could be so small that the effluent flows onto the collecting plate without forming droplets but the solvent is, nevertheless, flash-evaporated.

A preferable approach to suppress splashing and other problems, however, is to atomize the effluent such as by using an ultrasonic atomizer, preferably of the non-pneumatic and non-electrostatic type (for safety). If such a nozzle is used, then the inert gas flow pattern in the vacuum oven preferably is designed so that the atomized particles are channeled only toward the collecting plate.

In any case, so long as the droplets are confined to falling on the collecting plate, smaller droplets are preferred to enhance evaporation.

The improved system of this invention can be used with either homogeneous or heterogeneous solutions to study compositional variations in a complex chemical system as it emerges from the interfaced unit.

Although the examples which will be described hereinafter are based on fractionations using size exclusion chromatography, the interface unit can be adapted, with proper modifications and valvings, to other fractionations based on crystallinity differences (temperature elution fractionation), field flow fractionations (FFF), adsorption chromatography, or other arrangements which may involve homogeneous or heterogeneous polymer solutions or other mixtures.

DETAILED DESCRIPTION OF THE INVENTION

Figure 1:
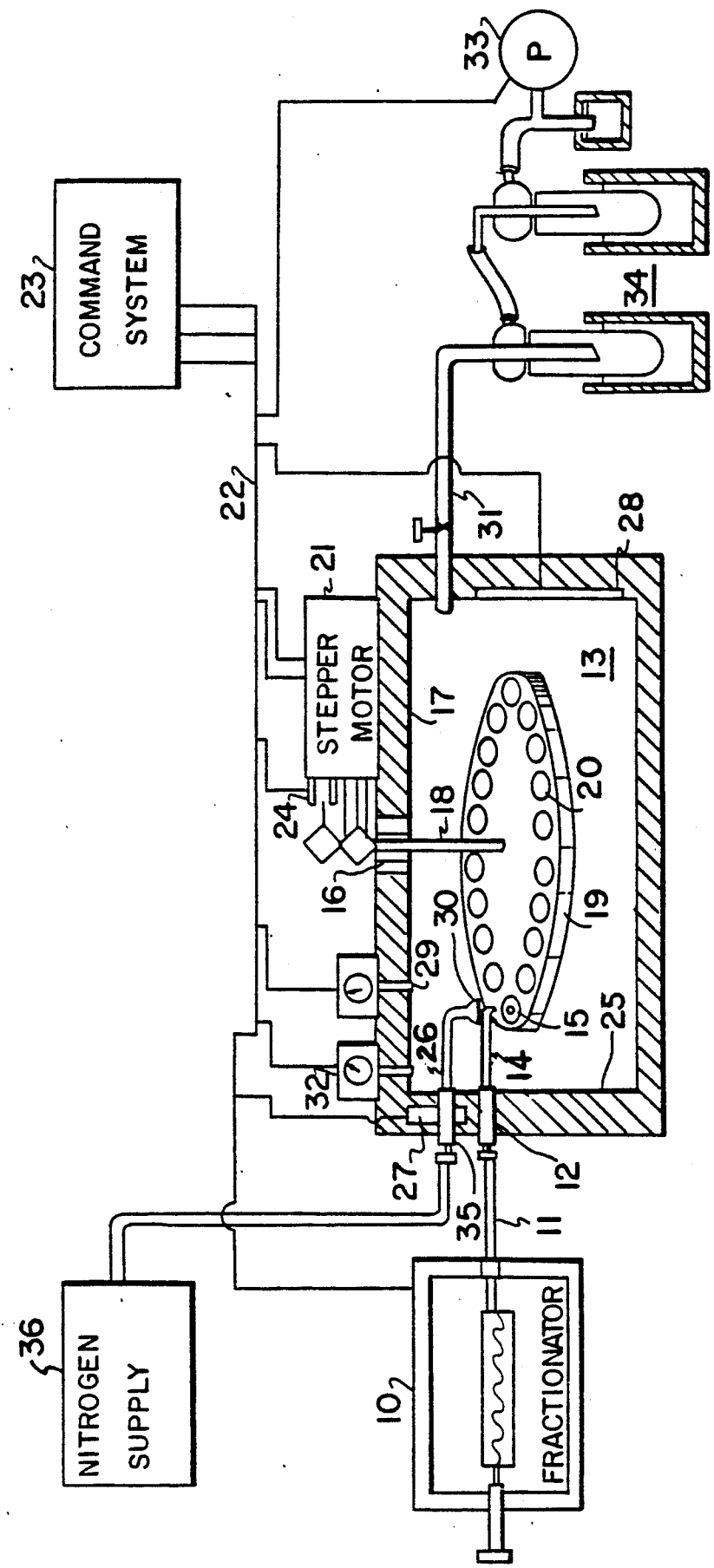
FIG. 1 is a schematic diagram, not drawn to scale, including a fractionator and an interface system constructed in accordance with the invention.

A schematic diagram, not drawn to scale, including a fractionator and an interface system according to the present invention, is shown in FIG. 1. The interface is relatively enlarged to show its details.

Referring to FIG. 1, a fractionator 10 such as a gel permeation chromatograph of a conventional and commercially available type such as a Waters Type 150-C GPC, is shown. Fractions of a sample of a material to be analyzed are provided in the form of a solute carried by a liquid solvent such as trichlorobenzene (TCB) via an outlet line 11. The outlet line 11 is connected to a sample inlet port 12 of a vacuum oven 13. An effluent sample supplying means 14, for example, stainless steel tubing of 0.009 inches inner diameter, extends from sample inlet port 12 to a point within oven 13 adjacent a sample collection station 15. Suitable valving (not shown) may be provided between outlet line 11 and sample inlet port 12 as needed to insure that liquid samples are provided at an appropriate rate at the collection station 15. It is preferable that small droplets be supplied to enhance the desired step of flash evaporation. Typically, oven 13 may have a capacity of 0.2 cubic feet and preferably is capable of being heated to a controlled temperature of the order of 200° C. Vacuum ovens which are available commercially (such as NAPCO Model 5831) may be modified so as to be suited for such use, provided there are no heating elements exposed on the inside of oven 13 or the oven may be constructed specifically for the present purposes. A hole having a vacuum seal 16 is provided in the center of the ceiling 17 of the oven 13 through which a shaft 18 is inserted. The shaft 18 is attached to a fraction collector 19 inside the oven 13. The fraction collector 19 is a disk of, for example, aluminum of 14.5 centimeters diameter. As will appear below, such a configuration is particularly suitable where subsequent FTIR analysis is to be performed. Holes are provided along the circumference of the disk to hold, for example, sixteen KBr (potassium bromide) plates, cups or vials 20. The shaft 18 is attached to a stepper motor unit 21 which is mounted externally on top of the oven 13. A power and logic signal cable 22 is connected from the stepper motor 21 to a command or control system 23 including, for example, a Compaq Computer. The position of the fraction collector 19 is sensed using a position sensor 24 (such as a fixed photocell and a slotted wheel connected to shaft 18). The position of the fraction collector 19 is controlled making use of the sensor 24, stepper motor 21, and the command system 23 (software commands) in a conventional closed loop position control arrangement.

Another hole is provided in the side wall 25 of the oven 13 to introduce a nitrogen line 26 which is connected to an external nitrogen supply 36. The nitrogen line 26 is associated with a heater 27 so that nitrogen provided via line 26 can maintain the desired temperature at the surface of the KBr cups 20, as required. Line 26 may be coaxial with tubing 14, (surrounding tubing 14) or may be separate from tubing 14. In the latter case, line 26 preferably is also made flexible or movable to adjust the position of a blowing point 30.

A heater 28 is provided outside of oven 13 and a temperature sensing apparatus 29 (such as a thermocouple) is provided within oven 13 in the vicinity of collection station 15. The heater 28, temperature sensor 29 and command system 23 are coupled in a closed loop temperature control system. While the heaters 27 and 28 are shown as separate devices, in practice they may be parts of a single heater. A single heater arrangement may be advantageous in that the temperature of oven 13 and that of the blown nitrogen then may readily be maintained substantially equal. For safety reasons, it is preferable that the temperature of the hot nitrogen should not exceed that of oven 13.

Oven 13 is provided with a vacuum line 31 which extends inside of oven 13, a pressure (vacuum) sensing apparatus 32 connected to oven 13, and a vacuum pump 33 arranged to maintain the pressure within oven 13 at a predetermined level.

A dual cold trap 34 is associated with vacuum line 31 for collection of solvent evaporated within oven 13 as will be explained below.

The pressure sensing apparatus 32 is coupled to command system 23 to assist in maintaining the pressure (vacuum) within oven 13 in a predetermined range. The control arrangement preferably is configured so that if pressure and/or temperature exceed predetermined safety limits, warning signals are generated, power to the oven 13 is shut off and the chromatographic effluent is diverted away from the oven 13.

The geometry of the KBr collecting crystal 20 was found to be an important parameter. Flat KBr plates were found to be a less suitable collection media when the effluent is introduced as droplets. In that case, droplets of solution tend to flow to the edges of the plate 20 before the solvent evaporates. Consequently the collected sample (e.g., a polymer) deposits along the edges of plate 20 and it is difficult to get a good spectrum from such a sample. Therefore, the use of KBr cups 20 is often preferred. The latter act as a small "vial" and position the solute at the center of the cup 20.

If, on the other hand, flat KBr plates are to be used, then the GPC effluent should be applied to the plate 20 as a fine mist, using such devices as a non-electrostatic, ultrasonic atomizing nozzle (e.g. a Sono-Tek ultrasonic nozzle). The fine particle sizes of the atomized spray help the flash-evaporation, depositing a thin layer of fractionated material on the collection plate 20.

Depending on the particular circumstances, besides KBr cups, other collection media are possible. One possibility is the use of metal or glass cups containing suitable powders for diffuse reflectance measurements using normal accessories or microsampling devices. Another is to use a metal strip (with low infrared absorption characteristics) on which the material is deposited for subsequent surface analysis (e.g., using surface analysis techniques or microsampling accessories). A third possibility is to use tiny metal dishes for collecting fractions to be analyzed using a mass spectrometric technique, for example.

The apparatus according to this invention can be miniaturized, converted to a continuous on-line process analyzer using the dual chamber configuration described above, or used as an interface device for other types of analytical techniques. In particular, a grid type design, typical of some fraction collection devices, is an alternative. If the interface is to be used for on-line process analysis, then the details of the oven and that of the collecting medium are likely to be changed.

During a run, the vacuum oven 13 is maintained at a high enough temperature and vacuum to allow the solvents to flash evaporate as they come in contact with the KBr dish 20. The effluent to be sampled (e.g. GPC effluent) is directed into the oven 13 through the stainless steel tubing 14 inserted through the vacuum-tight opening on the sidewall of the oven 13. Although this tubing 14 may be externally valved for proper flow-rate control, it was not needed for the experiments described herein.

The effluent enters the oven 13, and falls on the KBr cups 20 drop-by-drop at a flow rate of, for example, 0.5 milliliters per minute. In order to assure that each droplet immediately loses its solvent, the temperature and pressure of the oven 13 should be adjusted, depending on the boiling point/vapor pressure characteristics of the solvent to be eliminated. For example, if TCB is the solvent, the temperature-pressure relationship given below should be consulted.

TABLE

| Vapor pressure of TCB | | | | | | |
|---|---|---|---|---|---|---|
| Vapor pressure (mmHg) | 760 | 400 | 100 | 40 | 10 | 5 | 1 |
| Temperature (°C.) | 213.0 | 187.7 | 140.0 | 114.8 | 87.7 | 67.3 | 38.4 |

This relationship establishes a minimum temperature needed for evaporation of a single drop, but actual temperatures in oven 13 should be maintained above the theoretical value by, for example, at least 40° C. to insure efficient evaporation of many drops falling on the same cup 20. This additional temperature increment is required since the heat of vaporization will drop the temperature of the cup 20 below the boiling point of the solvent (under the given conditions). To insure the cup 20 is hot enough throughout the collection stage, the temperature of oven 13 should therefore be maintained higher than the theoretical boiling point of the solvent, and/or one must provide an additional source of heat directly to the cup surface.

With TCB as the chromatographic solvent, a stream of hot nitrogen blowing over the collecting cup 20 was found to be beneficial, and at the same time effectively eliminated splashing problems. The heated nitrogen was introduced via the flexible metal tubing 26. The temperature of the nitrogen is controlled by means of a thermocouple (not shown) placed after the heating cartridge 27. The tip of the nitrogen line 26 may be equipped with a baffle to control the size of the heated area. Alternatively, a perforated toroidal (ring-shaped) nozzle may be employed to provide a uniform cylindrical jet of inert gas at the sample collection station 15.

As droplets fall on a cup 20 at collection station 15, and the solvent immediately flashes off, the cup 20 will contain the fractionated residue. The flashed-off solvent is continuously carried away from the vacuum oven via vacuum line 31 into cold trap 34 where the solvent is condensed. Cold trap 24 is emptied on a regular basis. After a fraction is collected, the carousel 19 moves to the next position, and so on. It was found that sample quantities as small as one microgram were sufficient for subsequent FTIR analysis. The residence time at each position is either preset or triggered, depending on the experimental setup and the distribution pattern of the chromatographic information (ie. continuous or discrete signals). If an ultrasonic atomizer is used, especially of the non-electrostatic type, then the nozzle-to-plate distance is adjusted, depending on the desired pattern of the sprayed material. The nozzle geometry and the ultrasonic frequency can also be adjusted to control the spray pattern or the spot size. To assure that the atomized mist emerging from the nozzle is channeled entirely toward the collecting plate 20, the vacuum port 31 preferably is positioned beneath the carousel 19, and preferably beneath plate 20 at collection station 15. If the latter option is chosen, then additional openings on the carousel 19, in the vicinity of plate 20, will assure a uniform flow of heated nitrogen around the plate 20. In addition, a cylindrical jet of hot nitrogen in the direction of the plate 20, and of a chosen diameter, will further channel or direct the atomized particles emerging from the nozzle toward plate 20 only.

After the collection is over, the temperature of the oven 13 is brought down and the vacuum broken. The carousel 19 is now ready for composition analysis using selected microanalytical techniques. Since FTIR was contemplated in this case, the carousel 19 is detached from shaft 18, removed from the oven 13 and placed into the auto sampler assembly of the FTIR spectrometer (into which it is designed to fit) to automatically record the spectra of the collected samples.

An interface system of the type shown in FIG. 1 was connected to a GPC (Waters, Inc., Type 150-C) and the effect of the vacuum on the flow rate and the system pressure was examined. It was found that the flow rate in the GPC is not at all affected by the pressure drop in the vacuum oven 13 at 1 mm Hg as compared to 760 mm Hg.

Experimental details

Figure 2:
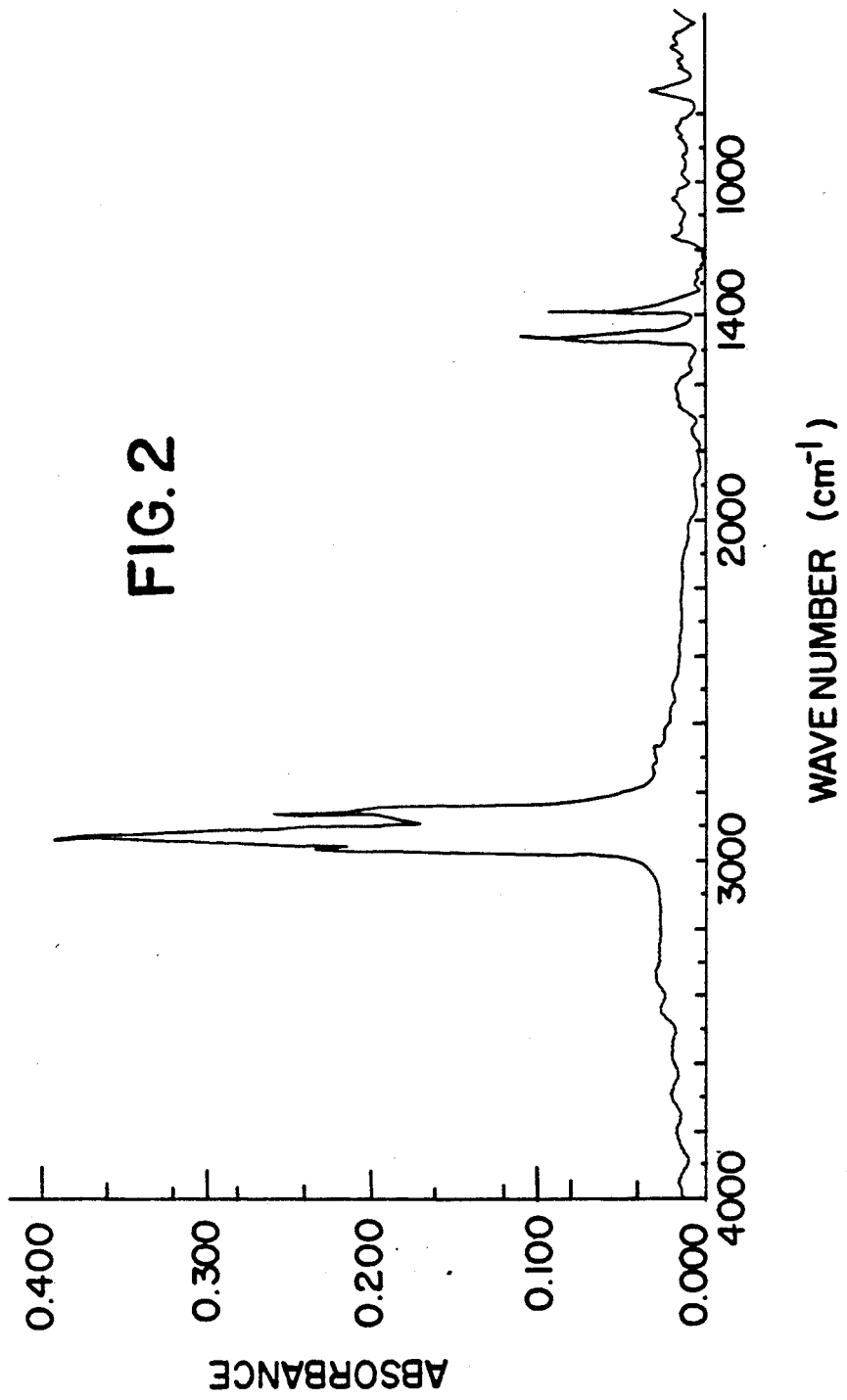
FIG. 2 is a Fourier Transform Infrared (FTIR) spectrum of an ethylene-propylene rubber residue collected utilizing an apparatus of the type shown in FIG. 1.

In the experiment, first, a 0.6 weight percent solution of EPR was prepared in TCB and 100 microliters of this solution was injected into the GPC coupled to the interface system of the type shown in FIG. 1. The column temperature was maintained at 120° C., flow rate at 0.5 ml/min. The pressure of the oven 13 was maintained at 40 mm Hg, while its temperature was about 150° C., with a gentle flow of $N_2$ through the system. The operation of the interface system was observed. The effluent was continuously flash evaporated in the interface oven 13 and a thin film of the EPR residue was formed on a KBr cup 20 (13×2 mm). The FTIR spectrum of the sample was recorded and is shown in FIG. 2. Similar experiments were performed successfully with ethylene-vinyl acetate (EVA) copolymers.

In the FTIR spectrum shown in FIG. 2, not only a C—H stretching region at about 2800-3000 $cm^{-1}$ but also a bending region at about 1400 $cm^{-1}$ can clearly be observed. Based on experiments similar to those described above, the detectability limit of the method was investigated. It was found that one microgram of sample is sufficient to permit quanitative analysis. With typical concentrations of the low and high ends of the GPC effluent of the order of $10^{-6}$ grams per milliliter, if ten fractions are collected for each sample, the collection period will be about two minutes per fraction and the deposition amounts of sample at the extremes will be about one microgram (minimum). A residue of, for example 6.6 micrograms would display an excellent signal-to-noise ratio.

In two separate experiments, seven fractions were collected from each of two rubbers. The oven temperature was maintained at 130° C., oven pressure was in the vicinity of 5-10 mm Hg, and the nitrogen flow rate was about 0.3 cc/minute.

The movements of carousel 19 were timed based on an analysis of the elution time profile from a previous chromatogram of the same material utilizing a conventional differential refractometer (DRI). During the actual fraction collection, the DRI detector was bypassed.

To adjust the temperature and the pressure of the oven 13 to assure smooth flash-evaporation and eliminate splashing problems, an external source of heated nitrogen 36 was introduced into the system and directed at the sample-collection site 15. Although this additional flow calls for a slight sacrifice in the vacuum of the oven 13, the loss is small, since it could bring the vacuum from 1 mm to 5 mm Hg or higher. From standard temperature-pressure tables, it appears that 1-5 mm Hg vacuum at 50°-70° C. would be a minimum vacuum to accomplish the task. Actual oven temperatures should be maintained 30°-50° C. higher than the theoretical evaporation point to account for any heat of vaporization at the collector position 15. The flashed-off solvents were collected in the dual cold trap 34.

The amount of polymer deposited in each dish 20 will depend on the particular fractionation and polymer system studied. For instance, if ethylene-propylene copolymers are fractionated on a GPC column at a temperature of 130°-150° C., using trichlorobenzene as a solvent, the average weight of the deposit will be in the 1-50 microgram range. Under these conditions, good quantitative FTIR spectra are obtained.

Figure 3:
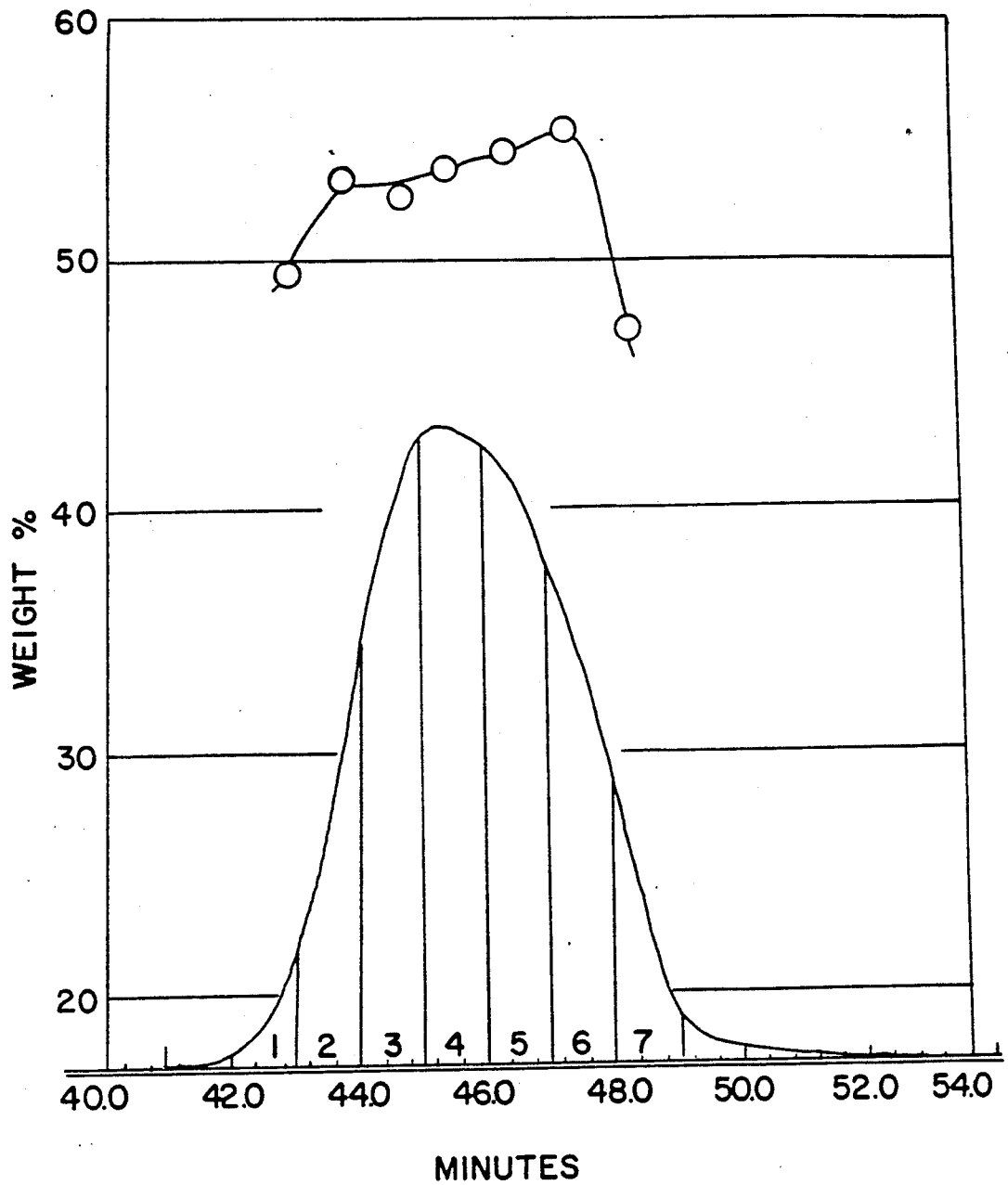
FIG. 3 illustrates a CD profile (upper trace) and gel permeation chromatogram (lower trace) for one type of ethylene-propylene rubber (EPR) which was analyzed employing this invention.

The two EPR samples were fractionated using the apparatus of FIG. 1. The spectra of the collected fractions were obtained by placing the carousel 19 into the autosampler of an FTIR spectrometer. From the spectra, the percent ethylene of each fraction was calculated. The retention time vs. percent ethylene profile is shown in the upper trace of FIG. 3 for the first sample. The vertical lines on the GPC curve show the timing of the fraction collection. The ease of obtaining such CD information is unprecedented. The higher molecular weight samples are retrieved earlier (lower trace-left hand end) while the lower molecular weight samples are retrieved later.

Figure 4:
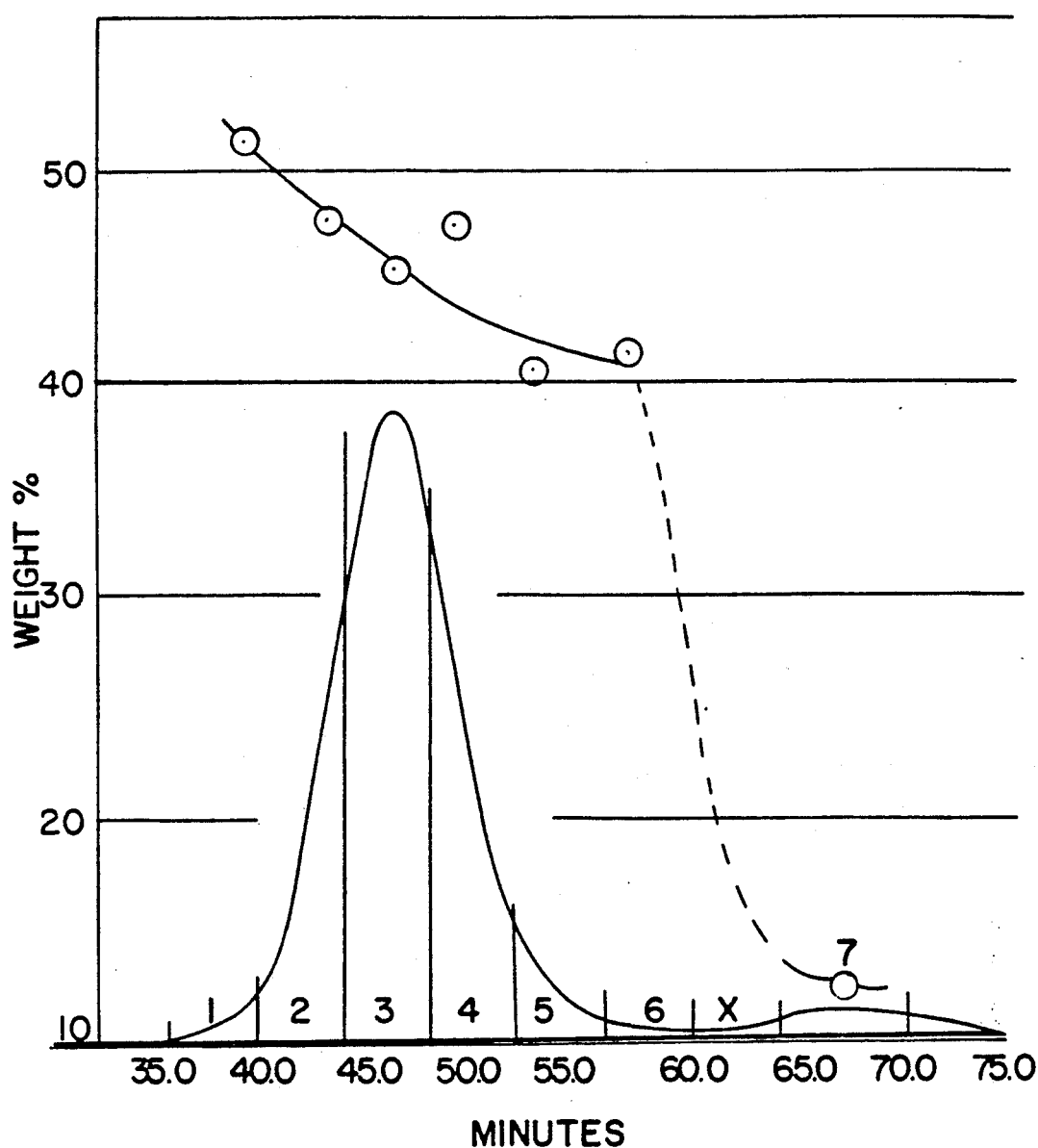
FIG. 4 illustrates a CD profile (upper trace) and gel permeation chromatogram (lower trace) for a second EPR sample collected by the method of this invention.

The Ethylene CD for the second sample is shown in the upper trace in FIG. 4. In this case the percent ethylene decreases with decreasing MW. The presence of a low-ethylene content, low-MW fraction is evident from FIG. 4 (right hand end). Although these profiles were obtained from a single GPC fractionation, the extension to more complex cross-fractionations or solvent/non-solvent fractionations will readily be apparent to those engaged in this art.

Figure 5:
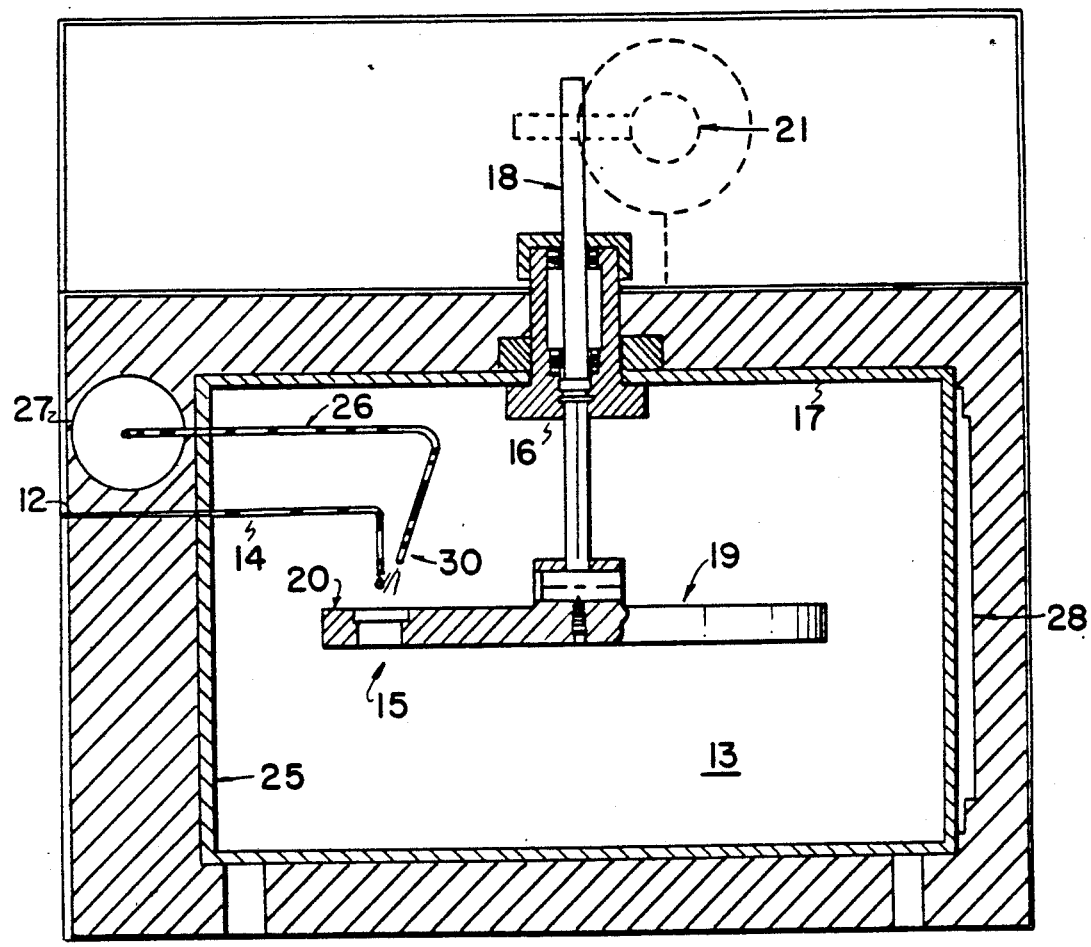
FIG. 5 illustrates in a cross-sectional view, an oven and associated apparatus constructed in accordance with this invention.

A more accurate representation of an oven 13 and associated components as explained above is shown in cross section in FIG. 5 wherein the same reference characters are used as in FIG. 1 for corresponding parts.

The concept of flash evaporating such high boiling solvents as TCB has been successfully demonstrated by means of the illustrated apparatus. It could be used for further investigation of structure-property relationships.

While the apparatus described above may be implemented utilizing various arrangements of commercially available hardware elements or may be custom designed according to a particular application, one set of readily usable controller components which was obtained from Cybernetic Microsystems of San Gregoria, CA. comprises their Model CY525. Motor Controller, CY750 I/O Controller, CY232 Serial Controller, CY300 LCD/Keyboard Controller, CY250 System Controller and CYB-002 Control Board.

In general, the sensing and control elements themselves may be constructed in a conventional manner (See, for example, the description of similar components in U.S. Pat. No. 4,604,363 referred to above).

The novel aspects of the foregoing method and apparatus are set forth in the following claims.

What is claimed is:

1. A method for the instantaneous generation of solute films through the fast evaporation of solvents from solutions carrying said solutes without excessively raising temperature of solution above the normal boiling point of solvent, comprising:

maintaining conditions inside a vacuum-oven interface, into which an ultrasonic nozzle and a fraction collection assembly is incorporated, below atmospheric pressure and at temperatures below the normal boiling point of the solvent, delivering said solution to the tip of said nozzle to break the solution up into fine droplets as the solution continuously emerges from said tip, channeling said droplets from said nozzle tip to specific sites on said collector assembly, evaporating solvent as said droplets migrate from said nozzle tip and continuously depositing for prespecified periods of time and at specific sites on said collector assembly, solvent-free solute films the spot size of which is determined by the nozzle-to-collector distance, moving said collector assembly at prespecified time intervals and number of steps to generate a particular pattern of solute deposits on a plurality of sites of said assembly for composition analysis.

2. A method for the instantaneous generation of solute films according to claim 1 wherein said solution originates from a process stream.

3. A method for the instantaneous generation of solute films according to claim 1 wherein said solute is fractionated prior to delivery to said nozzle.

4. A method for the instantaneous generation of solute films according to claim 2 wherein said fractionation is based on physical property differences.

5. A method for the instantaneous generation of solute films according to claim 3 wherein said fractionation is based on chemical property differences.

6. A method for the instantaneous generation of solute films according to claim 3 wherein said fractionation is based on combination of physical and chemical property differences.

7. A method for the instantaneous generation of solute films according to claim 1 wherein the temperature within said oven is a predetermined increment above the ambient boiling point of solvent to the evaporation rate.

8. A method for the instantaneous generation of solute films according to claim 1 wherein said solution is delivered to said collector site at a volumetric rate and droplet size to permit the instantaneous evaporation of said solvent from said droplets.

9. Apparatus for the instantaneous generation of solute films through the fast evaporation of solvents from solutions carrying said solutes without excessively raising temperature of solution above the normal boiling point of solvent, comprising:

a vacuum-oven into which an ultrasonic nozzle and a fraction collection assembly is incorporated, means for maintaining conditions inside said vacuum-oven below atmospheric pressure, means for delivering said solution to the tip of said nozzle to break solution up into fine droplets which are channeled to specific sites on said collector assembly, a plurality of collection sites on said fraction collector assembly to collect solvent-free solute films the spot size of which is determined by the nozzle-to-collector distance, means for moving said collector assembly at prespecified time intervals and number of steps to generate a particular pattern of solute deposits on plurality of sites of said assembly for composition analysis.

* * * * *